United States Patent [19]

Kumar

[11] 4,331,131
[45] May 25, 1982

[54] METHOD FOR TREATING CARCINOMA OF THE UTERINE CERVIX

[75] Inventor: Pullatikurthi P. Kumar, Omaha, Nebr.

[73] Assignee: The Board of Regents of the University of Nebraska, Lincoln, Nebr.

[21] Appl. No.: 104,358

[22] Filed: Dec. 17, 1979

[51] Int. Cl.³ .............................................. A61N 5/00
[52] U.S. Cl. ...................................................... 128/1.2
[58] Field of Search ................................... 128/1.1, 1.2

[56] References Cited

U.S. PATENT DOCUMENTS

| 2,516,261 | 7/1950 | Schutt | 128/1.2 |
| 2,544,939 | 3/1951 | Ritala | 128/1.2 |
| 3,060,924 | 10/1962 | Rush | 128/1.2 |
| 3,807,386 | 4/1974 | Rocoplan et al. | 128/1.2 |

FOREIGN PATENT DOCUMENTS 298152  3/1972  U.S.S.R. ............................... 128/1.2

*Primary Examiner*—Kyle L. Howell
*Attorney, Agent, or Firm*—Vincent L. Carney

[57] ABSTRACT

Disclosed is a method for treating carcinoma of the uterine cervix by judiciously applying radioactive material immediately adjacent the uterine cervix for an extended period of time empirically determined by the radiologist. The novel method comprises inserting three radioactively chargeable components including a central tubular tandem vaginally longitudinally into the uterine cervix and two non-lineal tubular ovoidal assemblies longitudinally locatable at the cervix and positioned laterally between the respective vaginal walls and the uterine cervix. The ovoidal assemblies are conveniently removably and pivotably connected to the central tandem component externally of the vagina along the sagittal plane through a novel adapter member whereby the radioactively chargeable ovoidal assemblies tend to remain within a laterally extending plane located substantially midway the transversely separated vasicovaginal and rectovaginal septa, even though the patient periodically shifts her reclining posture during the extended treatment by said vaginally protruding apparatus.

10 Claims, 13 Drawing Figures

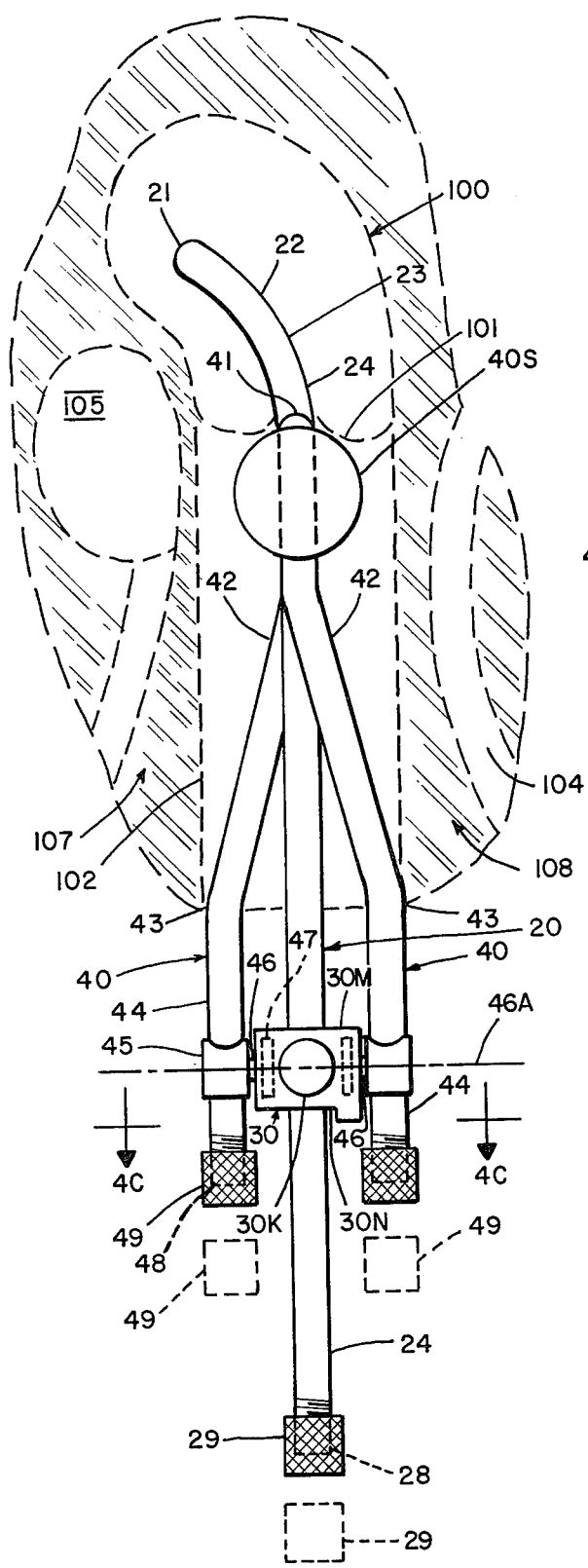
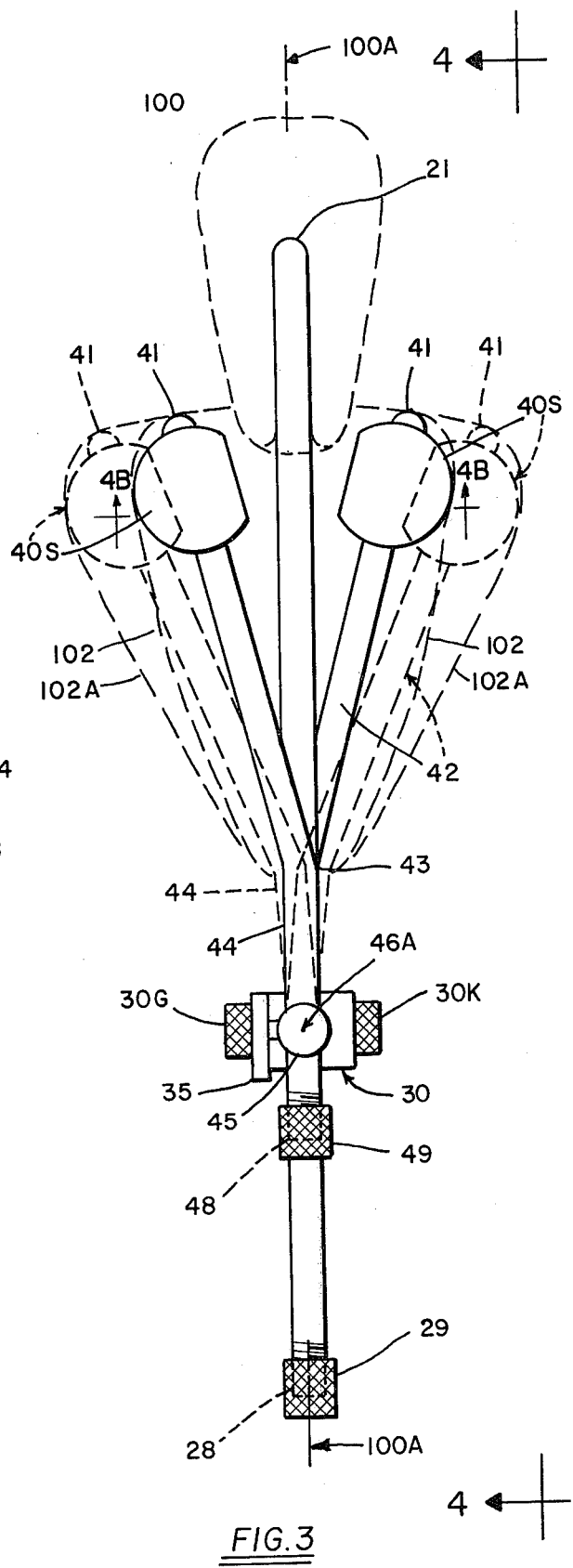
FIG. 4
FIG. 3

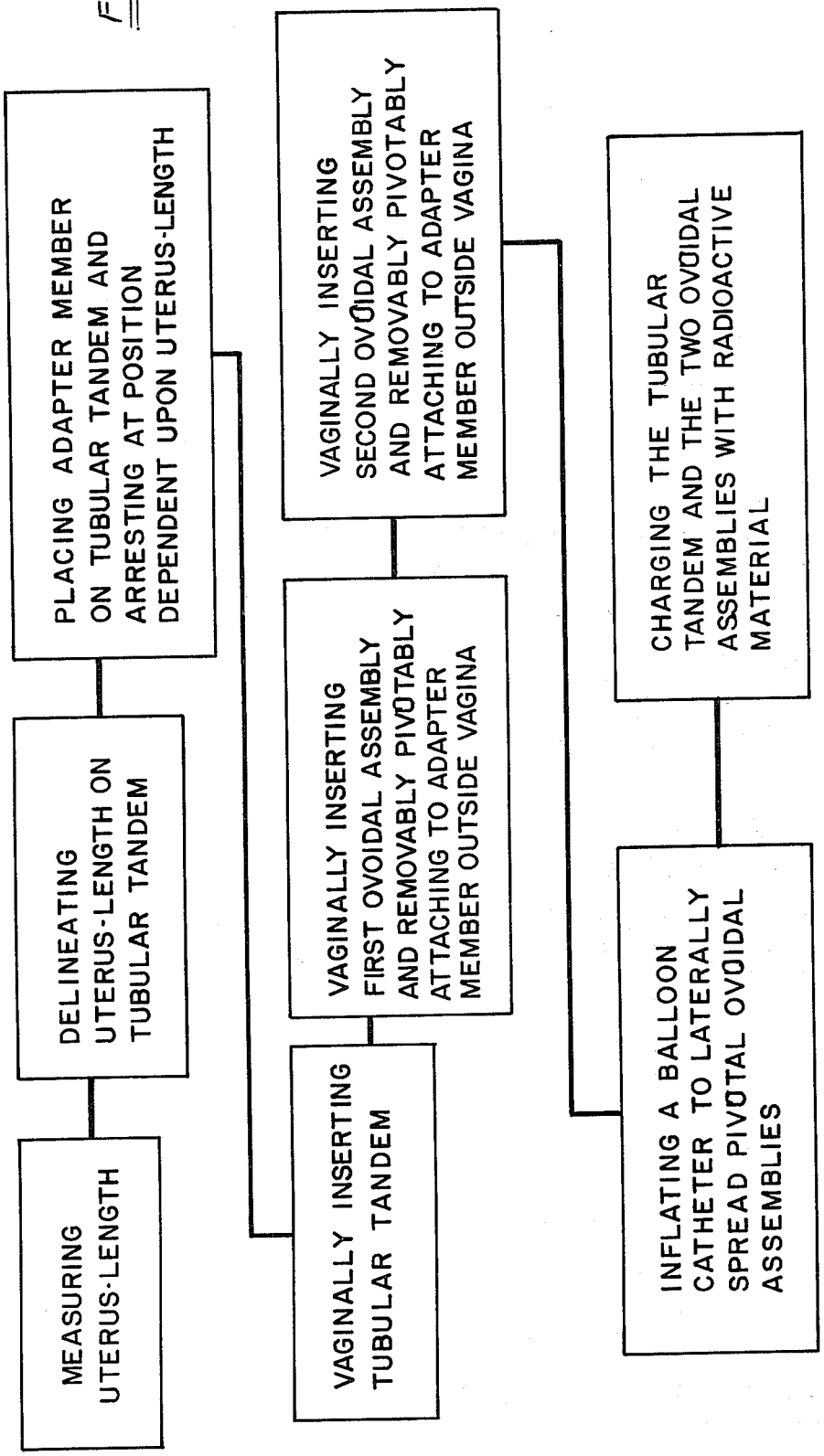

METHOD FOR TREATING CARCINOMA OF THE UTERINE CERVIX

BACKGROUND OF THE INVENTION

For a number of years, carcinoma of the uterine cervix has been treated by applying radium or other radioactive material immediately adjacent to the uterine cervix for an extended duration of at least 24–48 hours, empirically determined by the attending radiologist. Prior art apparatus for such treatment comprises for the radioactively chargeable components a central tubular tandem vaginally insertable longitudinally into the uterine cervix and two ovoids longitudinally locatable at the cervix and laterally positioned between the cervix and the respective vaginal walls. Inasmuch as uterine cervix carcinoma typically spreads to both lateral sides of the cervix, the two longitudinally aligned ovoids are necessarily employed on opposite lateral sides of the cervix-entering central tandem.

Radiological practitioners have recognized that whenever radioactive treatment is employed for carcinoma of the uterine cervix, extreme care must be taken to minimize radiation of the transversely separated vasicovaginal and rectovaginal septa, said septa being longitudinally aligned and sagittally coplanar with the uterine cervix, otherwise, radiation might cause septa fistulae whereby urine and/or fecal matter will leak into the vagina. However, transverse directional restriction of the radioactively charged and laterally separated ovoids to an ideal location midway the transversely separated vulnerable septa during patient treatment has eluded the radiological arts. This problem has troubled the art primarily because the extra-vaginally protruding trailward parts of the laterally separated ovoids tend to spread the vaginal labia laterally and the reclining patient cannot avoid changing her reclining posture positions during the extended treatment period. Obviously, nearly every change in reclining posture by the patient involves thigh movement which disturbs the positions of the externally protruding and divergent ovoid assemblies of the prior art. Accordingly, the transverse location of the respective radioactively charged ovoids is apt to be shifted in one or the other transverse direction resulting in inimical radioactive exposure to the vasicovaginal and rectovaginal septa and in insufficient radioactive treatment to the cervical carcinoma.

OBJECTS

It is accordingly the general objective of the present invention to provide a method for treating carcinoma of the uterine cervix by applying radioactive material for an extended period of time immediately adjacent to the cervix and with practically no accompanying exposure to the vasicovaginal and rectovaginal septa.

It is an ancillary general objective of the present invention to provide a clinical method wherein the ovoids are made to remain within a laterally extending plane located substantially midway the transversely separated vasicovaginal and rectovaginal septa, even though the reclining patient periodically shifts her thigh positions during the extended treatment period by said extra-vaginally protruding apparatus.

It is another object of the present invention to provide clinical methods which facilitate the accurate placement of the radioactive material and with minimal likelihood that radioactively sensitive anatomical parts will be inimically exposed.

It is a further object to provide a method which is amenable for use with numerous patients regardless of vaginal and uterine characteristics.

SUMMARY OF THE INVENTION

With the above and other objects and advantages in view which will become more apparent as this description proceeds, the applicator apparatus used in treating carcinoma of the uterine cervix generally comprises; a tubular tandem generally longitudinally extending along a sagittal plane and having a finite tandem-length defined by a closed lead-end for insertion longitudinally through the uterine cervix and a closeable trail-end permitting eventual charging of radioactive material into the tandem leadward length portion; an adapter member arrestably slidably surrounding the tubular tandem; and two ovoidal assemblies each comprising an elongated tubular arm having a longitudinal finite arm-length less than said tandem-length and defined by a closed leading-end and a closeable trailing-end permitting eventual charging of radioactive material into the arm leading portions, each said ovoidal assembly also comprising an ovoid type spacer means removably surrounding the arm substantially at its leading-end, each said ovoidal assembly being removably pivotably attachable to the adapter member through a transversely extending pivot means located relatively near to the arm trailing-end, there being septa protection means that restrains the laterally movable arms' leading-ends within a mid-plane perpendicular to the sagittal plane and located substantially midway the vasicovaginal and rectovaginal anatomical septa.

BRIEF DESCRIPTION OF THE DRAWINGS

In the drawings, wherein like characters refer to like parts in the several views, and in which;

FIG. 3 is a top plan view of the preferred embodiment applicator apparatus of the present invention and superimposed upon the environment of FIG. 1; the bottom plan view of the applicator apparatus (not shown) is a mirror image thereof;

FIG. 4 is a leftward side elevational view of the preferred embodiment applicator apparatus taken along line 4—4 of FIG. 3, and hence, superimposed upon the anatomical environment of FIG. 2; the rightward side elevational view is a mirror image thereof;

FIG. 8A (not shown) is a mirror image of FIG. 8 taken along line 8A—8A of FIG. 5;

FIG. 10 is a flow diagram alluding to the method for treating uterine carcinoma and employing the applicator apparatus of the present invention.

DESCRIPTION OF THE ANATOMICAL ENVIRONMENT

Figure 2:
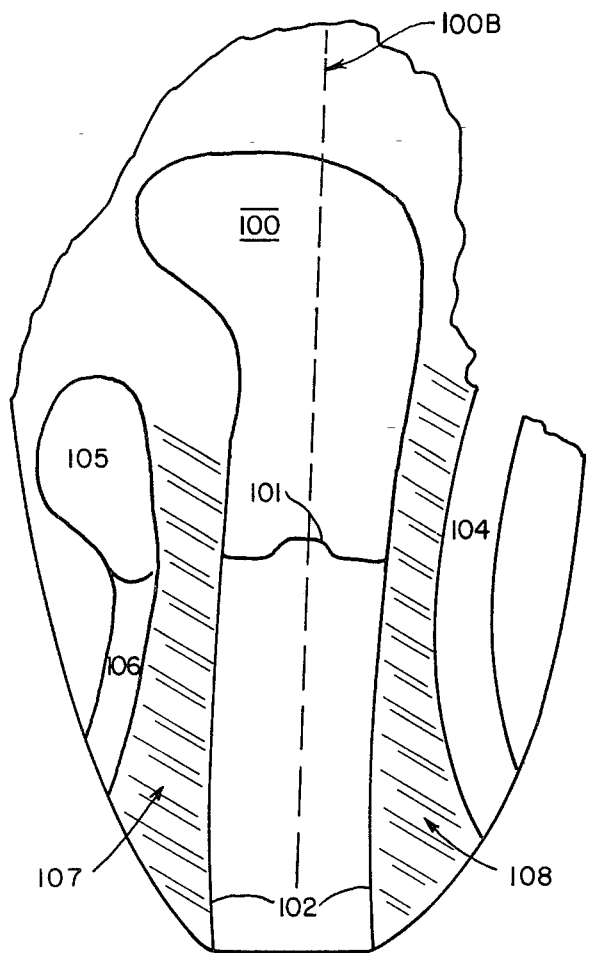
FIG. 2 is a sectional elevational view taken along the sagittal plane i.e. along line 2—2 of FIG. 1, whereby the vasicovaginal and rectovaginal septa and the laterally extending mid-plane (100B) of the anatomical environment are revealed.
Figure 1:
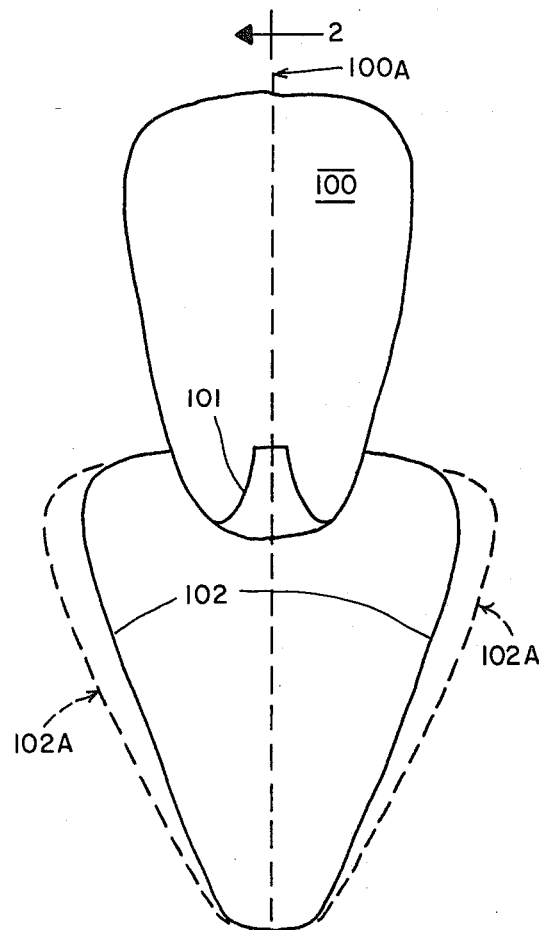
FIG. 1 is a schematic plan view of the uterine and vaginal anatomical environment at which the apparatus and method of the present invention is employed.

Referring initially to FIGS. 1 and 2, reference character 100 refers to the female uterus having cervix 101, and the reference character 100A refers to the anatomical sagittal plane. The laterally distensible (102A) vaginal walls 102 commencing from vaginal orifice 103 merge with uterus 100. Between the bladder 105 and vaginal wall 102 is the vasicovaginal septum 107, and between the rectum 104 and a vaginal wall 102 is the rectovaginal septum 108. As is well known in the prior art, radioactive exposure to the vasicovaginal septum 107 and to the rectovaginal septum 108 is to be avoided during radioactive type treatment of uterine cervix (101) carcinoma.

DESCRIPTION OF PREFERRED EMBODIMENT APPARATUS

Figure 4B:
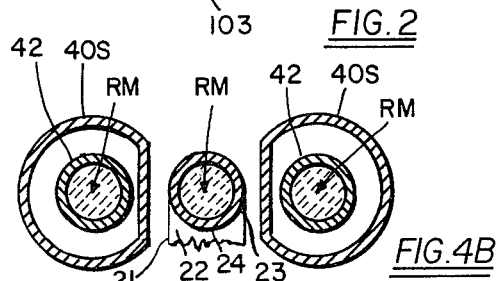
FIG. 4B is a sectional elevational view taken along line 4B—4B of FIG. 3.

The preferred radioactive treatment applicator apparatus 10 of the present invention generally comprises a longitudinally (100A) extending tubular tandem 20 having a finite tandem-length parallel said sagittal plane 100A and defined by a closed lead-end 21 and a closeable trail-end 28. When tubular tandem 20 is inserted longitudinally through vaginal orifice 103, lead-end 21 is ultimately positioned inside uterus 100. Tubular tandem 20 at trail-end 28 is closeable e.g. with a removable cap 29, to pemit charging of radioactive material "RM" at lead-end 21. Inasmuch as uterus 100 slopes somewhat transversely forwardly (as seen in FIGS. 2, 4, and 5), tandem leadward portion 22 also slopes forwardly; reference character 23 represents the confluence of leadward portion 22 and the co-sagittal lineal trailward portion 24.

There is an adapter member e.g. 30, slidably surrounding the tubular tandem trailward portion 24 and including releasable arresting means e.g. set-screw 30K, for empirically establishing the adapter member 30 at the clinically selected longitudinal position between the tandem lead-end 21 and trail-end 28. As will be explained later in greater detail, the twin ovoidal assemblies 40 are removably pivotably associated with adapter member 30 so as to pivot about transversely extending pivot-axis 46A only whereby the leading-end 41 (containing radioactive material "RM") is forcibly restrained within a laterally extending mid-plane 100B perpendicular to sagittal plane 100A and located substantially midway the transversely separated vasicovaginal (107) and rectovaginal (108) septa.

Each of the two twin ovoidal assemblies 40 comprises an elongated tubular arm 40T having a longitudinally (100A) extending finite arm-length less than the tandem-length and defined by a closed leading-end 41 and a closeable trailing-end 48. Each tubular arm 40T is inserted alone longitudinally through vaginal opening 103 until its leading-end 41 is positioned co-elevational with uterine cervix 101, though ultimately movable along mid-plane 100B from cervix 101 against distensible vaginal wall 102-102A. Respective tubular arms 40T at trailing-end 48 are closeable e.g. with a removable cap 49, to permit charging of radioactive material "RM" at leading-end 41. Each said tubular arm 40T is also provided with an ovoid type spacer means 40S removably surrounding arm 40T substantially at its leading-end 41 to maintain some finite spacing between the radioactive material "RM" and anatomical parts 100–102.

Figure 4C:
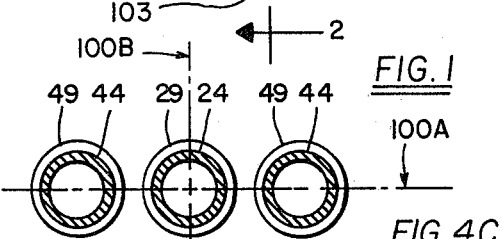
FIG. 4C is a sectional elevational view taken along line 4C—4C of FIG. 4.
Figure 6:
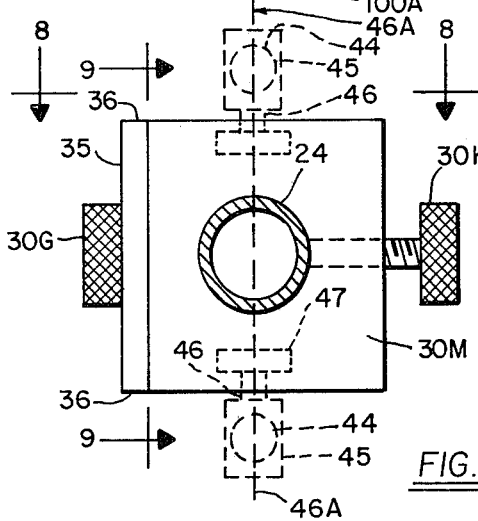
FIG. 6 is a sectional elevational view taken along lines 6—6 of FIGS. 5, 8, and 9.
Figure 5:
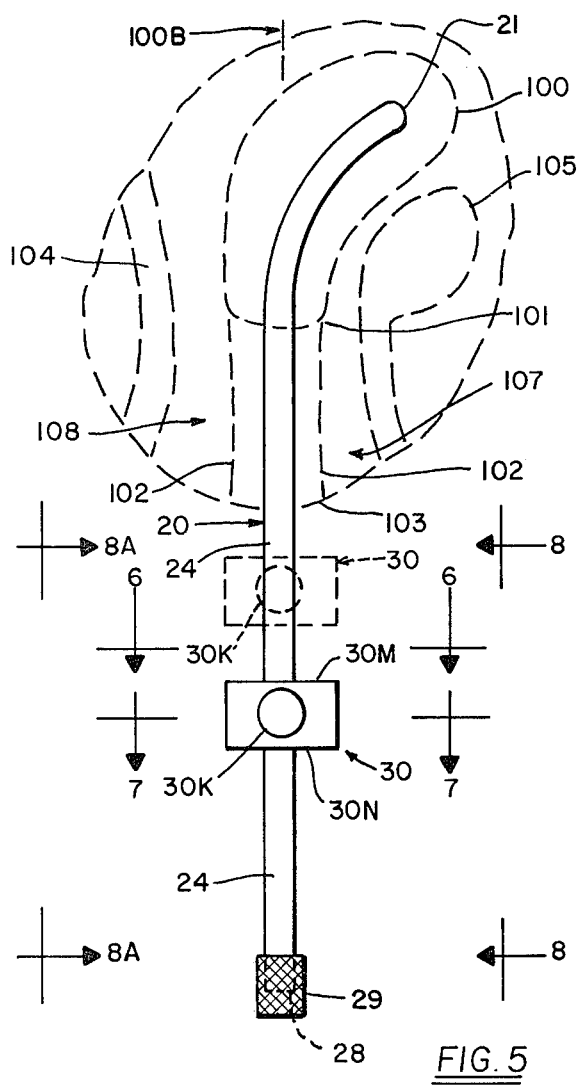
FIG. 5 is a rightward side elevational view of the tubular tandem are arrestably slidably associated adapter member portions of FIG. 4.

As seen in FIGS. 3 and 4C, the trail-length 44 of each ovoidal assembly arm 40T, as well as the tandem trailward-length 24, lie parallel the sagittal plane 100A. This sagittal-co-parallel relationship is important for two reasons. First, it does not exert appreciable lateral pressure at the vaginal entrance 103 and walls 102 whereby the patient is relatively comfortable during her extended period of radioactive therapy by apparatus 10. Second, thigh movements by the patient during her extended treatment period will not shift the radioactively charged arms leading-end 41 toward the vulnerable septa 107 and 108. As previously alluded to, each said ovoidal assembly 40 is removably pivotably attachable to the adapter member 30 through a transversely extending (46-46A) pivot means whereby the arm leading-end 41 and spacer means 40S thereat are forcibly restrained within said laterally extending mid-plane 100B; however, the spacers 40S and leading-ends 41 are permitted to move laterally away from uterine cervix 101 against distended vaginal walls 102A. For the purposes stated in this paragraph, and as alluded to in FIGS. 3, 4, and 4A, each tubular arm 40T has a lead-length 42 and a trail-length 44 merging together at permanent bend 43; leadward-length 42 toward lead-end 41 lies substantially parallel mid-plane 100B and the trailward-length 44 lies substantially parallel to sagittal plane 100A. Though the planes 100A and 100B are perpendicular to each other, arms' length segments 42 and 44 are made respectively parallel to planes 100B and 100A by providing the permanent bend 43 in each elongated tubular arm 40T.

Figure 7:
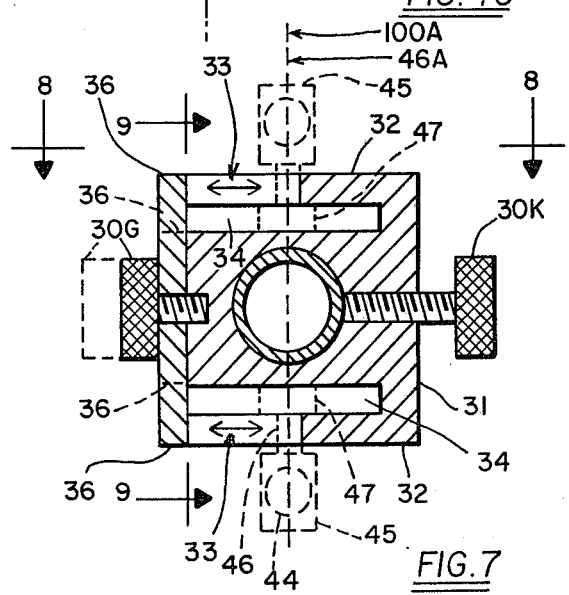
FIG. 7 is a sectional elevational view taken along lines 7—7 of FIGS. 5, 8 and 9.
Figure 4A:
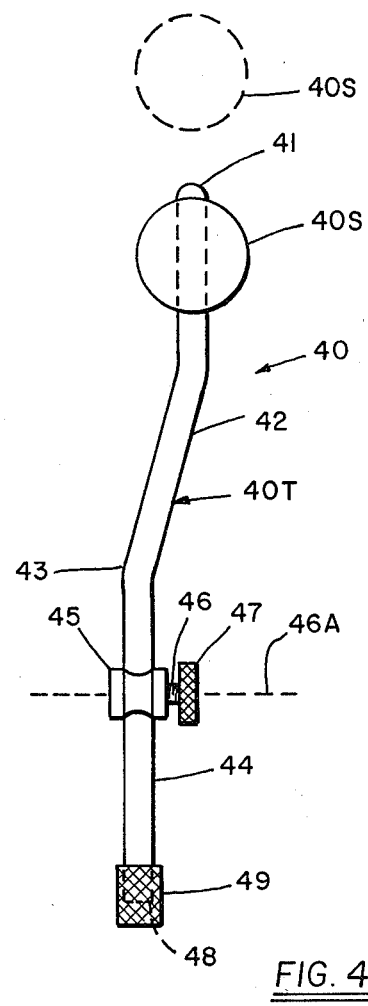
FIG. 4A is a leftward side elevational view of one of the two ovoidal assembly portions of FIG. 4, the second ovoidal assembly being a mirror image thereof.
Figure 8:
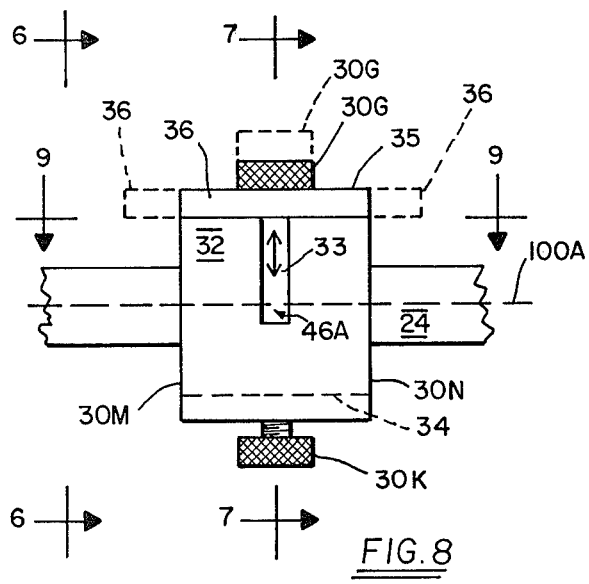
FIG. 8 is a sectional plan view taken along lines 8—8 of FIGS. 5, 6, and 7.
Figure 9:
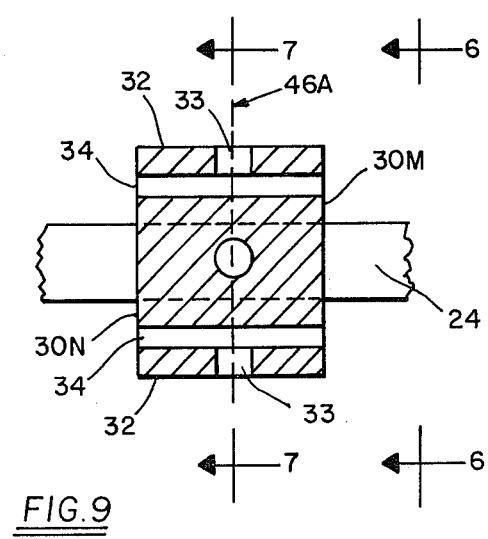
FIG. 9 is a sectional elevational view taken along lines 9—9 of FIGS. 6, 7, and 8.

Inasmuch as the leading-end 41 and hollow spacer 40S of each lead-length 42 must remain substantially parallel to mid-plane 100B as arms 40T are moving laterally from uterine cervix 101 to opposite vaginal walls 102A, the transversely extending pivot-axis 46A from adapter member 30 and the ovoidal assembly arm 40T preferably perpendicularly intersects arm trail-length 44 and mid-plane 100B. For example, as best seen in FIG. 4A, there might be a cylindrical collar 45 rigidly attached to and non-rotatably surrounding arm trail-length 44, axle 46 rigidly extending from collar 45 along pivot-axis 46A. That end of axle 46 remote from collar 45 might be equipped with a non-rotatable circular disc or flange 47. As will be explained later in greater detail, the tandem 20 is first anatomically emplaced as alluded to in FIG. 5; then, a single ovoidal assembly 40 is introduced through the vaginal opening 103 whereupon pivotal connection is effected between the adapter member 30 and ovoidal assembly 40; and finally, the second ovoidal assembly is anatomically introduced and pivotably attached to the adapter member in like manner. In keeping with such clinical method, the members 45–47 permit removable pivotal installation of the arms 40T to adapter member 30 by moving the anatomically emplaced arm 40T directionally laterally and parallel to mid-plane 100B, as indicated by double-headed arrows in the slots 33 shown in FIGS. 7 and 8.

The preferred adapter embodiment 30 shown in FIGS. 5-9 does permit the ready pivotal engagement therewith of ovoidal assemblies 40 by such directionally lateral movement of arms 40T by the physician. Adapter 30 slidably surrounds tandem trail-length 24 and includes; an upright lead-side 30M, an upright trail-side 30N, and an upright first-side 31. A set-screw 30K passing through transversely extending first-side 31 and bearing against tandem 20 provides an apt releasable arresting means for establishing the appropriate longitudinal position for the adapter member 30, as indicated in FIG. 5 phantom line. Adapter embodiment 30 also includes transversely separated parallel lateral-walls 32 overlying a laterally pair of laterally extending gaps or grooves 34 to accommodate the flanges 47. Lateral-walls 32 are respectively provided with a laterally extending central slotted portion 33 to accommodate the transversely separated and aligned axles 46. There are releasable locking means to prevent premature disengagement of the ovoidal assemblies 40 from the communicating lateral slots (33) and grooves (34), such as turnable gate 35 having parallel lineal edges 36. By virtue of set-screw 30G, gate 35 can be made to turn 90° as indicated in phantom line 36 in FIGS. 7 and 8, to permit uni-directional disengagement of both sets of pivot means 46-47 from the respective adapter seats 32-34.

CLINICAL METHODS FOR APPLICATOR APPARATUS

Clinical methods for utilizing the applicator apparatus concepts of the present invention comprise the following general steps:

A. measuring the longitudinal uterus-length with a sound instrument;

B. delineating the uterus-length along a tubular tandem (20) between the lead-end 21 and a balloon catheter surroundably positionable along the tubular tandem;

C. placing an adapter member (30) around the tandem (20), and releasably arresting (30K) the adapter at a longitudinal position located from the balloon catheter a distance substantially that of the longitudinal arm-length of an ovoidal assembly (40);

D. vaginally inserting th tubular tandem (20) into the patient whereby the lead-end 21 is inside the uterus, the balloon catheter is at the uterine cervix, and the adapter (30) is located externally of the vagina;

E. longitudinally inserting through the vagina a single ovoidal assembly (40) while maintaining the arm (40T) between the tandem (20) and the vaginal wall 102;

F. removably pivotably attaching the arm (40T) of said ovoidal assembly whereby the leading-end (41) is free to move only in a mid-plane 100B;

G. longitudinally inserting through the vagina a single ovoidal assembly (40) while maintaining the arm (40T) between the tandem (20) and the other vaginal wall 102;

H. removably pivotably attaching the arm (40T) of the said second ovoidal assembly whereby its leading-end 41 is free to move only in said mid-plane 100B;

I. inflating the balloon catheter whereby the leading-ends 41 of the respective ovoidal assemblies (40) are made to move in opposite lateral directions away from the uterine cervix until the spacer (40S) exerts firm pressure against the distended (102A) vaginal walls; and J. charging the tubular tandem (20) and the tubular arms (40T) with radioactive material. Preferably, the method also includes: moving the ovoidal assembly arms (40T) in the lateral direction to effect the required pivotal attachment (46-47) with the adapter seats (32-34); and followed by releasably (30G) locking both pivotal engagements (46-47) with a single turnable gate member (35).

From the foregoing, the construction and operation of the applicator apparatus and the methods for treating carcinoma of the uterine cervix will be readily understood and further explanation is believed to be unnecessary. However, since numerous modifications and changes will readily occur to those skilled in the art, it is not desired to limit the invention to the exact construction and method steps shown and described, and accordingly, all suitable modifications and equivalents may be resorted to, falling within the scope of the appended claims.

I claim:

1. A method of treating carcinoma comprising the steps of:

inserting a tubular tandem and first and second tubular side assemblies through the vaginal orifice with the tandem extending into the uterus and the first and second side assemblies being positioned against the vaginal wall; and emitting radiation from at least one of the tubular tandem and first and second tubular side assemblies;

the step of inserting the tubular tandem and first and second tubular side assemblies including the steps of inserting the tubular tandem with a mounting portion and a radiating portion attached to each other, inserting the first tubular side assembly with a first-tubular-side-assembly mounting portion and a first-tubular-side-assembly radiating portion attached together and inserting the second tubular side assembly with a second-tubular-side assembly mounting portion and a second-tubular-side assembly radiating portion attached together and with the mounting portions of each extending through the vaginal orifice in the sagittal plane and the radiating portions being located adjacent to the vaginal walls within a plane substantially perpendicular to the sagittal plane.

2. A method according to claim 1 in which the step of inserting includes the steps of:

first inserting the tandem into the uterus;

secondly inserting one of said first and second side assemblies through the vaginal orifice to a location in which the radiating portion is adjacent to the vaginal walls within a plane substantially perpendicular to the sagittal plane and mounting it in position with its mounting portion in the sagittal plane; and thirdly inserting the other of said side assemblies with its radiating portion in the plane perpendicular to the sagittal plane adjacent to the vaginal walls and mounting it with its mounting portion in the sagittal plane.

3. A method according to claim 2 in which the step of inserting includes the step of:

pivotally mounting the first and second side assemblies to said tandem by a pivot axis means lying within the sagittal plane; and pivotally holding said first and second side assemblies by mounting means for preventing rotation of the first and second side assemblies about their respective longitudinal axis while they pivot about said pivotal axis means.

4. The method according to claim 2 in which the step of radiating includes the step of inserting radioactive material into at least one of said tandem and first and second side assemblies after said tandem and first and second side assemblies have been inserted and mounted in place.

5. The method according to claim 4 in which the step of inserting includes the step of:
   pivotally mounting the first and second side assemblies to said tandem by a pivot axis means lying within the sagittal plane; and
   pivotally holding said first and second side assemblies by mounting means for preventing rotation of the first and second side assemblies about their respective longitudinal axis while they pivot about said pivotal axis means.

6. A method according to claim 1 in which the step of inserting includes the steps of:
   measuring the longitudinal uterus length;
   placing an adapter member around a tubular tandem having a straight portion with a slight curvature at its end;
   inserting the tandem through the vaginal opening with the curved end being inside the uterus and following the curvature of the uterus and the straight portion extending outside of the vaginal opening with the adapter being positioned outside the vaginal opening;
   inserting a first of the first and second side assemblies having a mounting portion and a radiation portion, with the radiation portion forming an obtuse angle with the mounting portion;
   pivotally attaching the mounting portion of the first inserted one of said first and second side assemblies to the mounting portion of the tandem by means of said adapter;
   inserting the other of said first and second side assemblies having a mounting portion and a radiation portion, with the radiation portion forming an obtuse angle with the mounting portion;
   mounting the mounting portion of said second inserted side assembly to the mounting portion of said tandem by said adapter; and
   moving the radiation portions of said first and second side assemblies in opposite directions within a plane perpendicular to the sagittal plane and with said mounting portion and radiation portion lying in the same plane and with the mounting portions of the first and second side assemblies and the tandem lying in the sagittal plane.

7. A method according to claim 6 in which the step of inserting includes the step of:
   pivotally mounting the first and second side assemblies to said tandem by a pivot axis means lying within the sagittal plane; and
   pivotally holding said first and second side assemblies by mounting means for preventing rotation of the first and second side assemblies about their respective longitudinal axis while they pivot about said pivotal axis means.

8. A method according to claim 1 in which the step of radiating from at least one of said tandem and first and second side assemblies includes the step of inserting into the tubular tandem and the first and second side assemblies a radioactive material after said tandem and first and second side assemblies are mounted into position.

9. A method according to claim 8 in which the step of inserting includes the step of:
   pivotally mounting the first and second side assemblies to said tandem by a pivot axis means lying within the sagittal plane; and
   pivotally holding said first and second side assemblies by mounting means for preventing rotation of the first and second side assemblies about their respective longitudinal axis while they pivot about said pivotal axis means.

10. A method according to claim 1 in which the step of inserting includes the step of:
   pivotally mounting the first and second side assemblies to said tandem by a pivot axis means lying within the sagittal plane; and
   pivotally holding said first and second side assemblies by mounting means for preventing rotation of the first and second side assemblies about their respective longitudinal axis while they pivot about said pivotal axis means.

* * * * *

UNITED STATES PATENT AND TRADEMARK OFFICE
CERTIFICATE OF CORRECTION

PATENT NO. : 4,331,131
DATED : May 25, 1982
INVENTOR(S) : Pullatikurthi P. Kumar Page 1 of 2

It is certified that error appears in the above—identified patent and that said Letters Patent is hereby corrected as shown below:

Column 1, line 28, change "cervix," to --cervix;--.

Column 2, line 11, change "comprises;" to --comprises:--.

Column 2, line 38, change "which;" to --which:--.

Column 2, line 65, change "are" to --and--.

Column 3, line 39, change "pemit" to --permit--.

Column 5, line 6, change "includes;" to --includes:--.

Column 5, line 43, change "th" to --the--.

UNITED STATES PATENT AND TRADEMARK OFFICE
CERTIFICATE OF CORRECTION

PATENT NO. : 4,331,131
DATED : May 25, 1982
INVENTOR(S) : Pullatikurthi P. Kumar It is certified that error appears in the above—identified patent and that said Letters Patent is hereby corrected as shown below:

Column 6, line 23, delete "and" after "wall;".

Column 6, line 26, insert "and" after "blies;".

Column 6, line 36, change "side assembly" to --side-assembly--.

Column 6, line 37, change "side assembly" to --side-assembly--.

Column 7, line 1, change "The" to --A--.

Signed and Sealed this

Fifth Day of October 1982

[SEAL]

Attest:

GERALD J. MOSSINGHOFF

Attesting Officer

Commissioner of Patents and Trademarks